United States Patent [19]
Sample et al.

[11] Patent Number: 5,618,293
[45] Date of Patent: Apr. 8, 1997

[54] SURGICAL INSTRUMENT

[75] Inventors: Philip B. Sample, Melrose, Mass.; Graham Smith, Plaistow, N.H.

[73] Assignee: Smith & Nephews Dyonics, Inc., Andover, Mass.

[21] Appl. No.: 471,226

[22] Filed: Jun. 6, 1995

[51] Int. Cl.⁶ ................................................. A61B 17/32
[52] U.S. Cl. .......................... 606/170; 606/180; 606/79; 128/753; 128/754
[58] Field of Search .......................... 606/79, 170, 180, 606/171, 183; 128/753, 754

[56] References Cited

U.S. PATENT DOCUMENTS

| | | | |
|---|---|---|---|
| 745,722 | 12/1903 | Freeman . | |
| 1,630,239 | 5/1924 | Binkley et al. . | |
| 1,636,636 | 1/1927 | Humble . | |
| 3,618,611 | 11/1971 | Urban | 128/305 |
| 3,847,154 | 11/1974 | Nordin | 128/305 |
| 4,020,847 | 5/1977 | Clark, III | 128/305 |
| 4,167,943 | 9/1979 | Banko | 128/305 |
| 4,167,944 | 9/1979 | Banko | 128/305 |
| 4,265,231 | 5/1981 | Scheller, Jr. et al. | 128/92 |
| 4,274,414 | 6/1981 | Johnson et al. | 128/305 |
| 4,306,570 | 12/1981 | Matthews | 128/754 |
| 4,320,761 | 3/1982 | Haddad | 128/305 |
| 4,445,509 | 5/1984 | Auth | 128/305 |
| 4,512,344 | 4/1985 | Barber | 128/305 |
| 4,517,977 | 5/1985 | Frost . | |
| 4,522,206 | 6/1985 | Whipple et al. | 128/312 |
| 4,541,423 | 9/1985 | Barber | 128/92 |
| 4,589,412 | 5/1986 | Kensey | 128/305 |
| 4,601,290 | 7/1986 | Effron et al. . | |
| 4,631,052 | 12/1986 | Kensey | 604/22 |
| 4,649,919 | 3/1987 | Thimsen et al. | 128/305 |
| 4,681,106 | 7/1987 | Kensey et al. | 128/305 |
| 4,696,667 | 9/1987 | Masch | 128/305 |
| 4,705,038 | 11/1987 | Sjostrom et al. | 128/305 |
| 4,760,848 | 8/1988 | Hasson | 128/340 |
| 4,770,174 | 9/1988 | Luckman et al. | 128/318 |
| 4,834,729 | 5/1989 | Sjostrom | 128/318 |
| 4,842,578 | 6/1989 | Johnson et al. | 604/22 |
| 4,867,155 | 9/1989 | Isaacson | 128/350 |
| 4,998,527 | 3/1991 | Meyer | 128/6 |
| 5,152,744 | 10/1992 | Krause et al. | 604/22 |
| 5,217,479 | 6/1993 | Shuler | 606/180 |
| 5,282,821 | 2/1994 | Donahue | 606/170 |
| 5,320,635 | 6/1994 | Smith . | |

FOREIGN PATENT DOCUMENTS

| | | |
|---|---|---|
| 0393834 | 10/1990 | European Pat. Off. . |
| 0445918 | 9/1991 | European Pat. Off. . |
| 0481760 | 4/1992 | European Pat. Off. . |
| 3828478 | 5/1989 | Germany . |
| 61-265133 | 11/1986 | Japan . |
| 1235321 | 6/1971 | United Kingdom . |

*Primary Examiner*—Michael Buiz
*Assistant Examiner*—Mark S. Leonardo
*Attorney, Agent, or Firm*—Fish & Richardson P.C.

[57] ABSTRACT

A surgical instrument includes a cutting implement comprised of two elements. A driver, which may be disposed within an outer member, transmits force applied at a base to the cutting implement to move one element of the cutting implement in one direction, and the other element in the opposite direction.

39 Claims, 5 Drawing Sheets

SURGICAL INSTRUMENT

BACKGROUND OF THE INVENTION

This invention relates to surgical instruments, and in particular to powered arthroscopic surgical instruments.

Powered arthroscopic surgical instruments typically include a rigid, stationary outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube along with irrigating fluid by the use of suction applied at the proximal end of the instrument. Examples of such surgical instruments are described in U.S. Pat. Nos. 4,203,444, 4,274,414, 4,834,729, and 4,842,578, all assigned to the present assignee and entirely incorporated herein by reference.

SUMMARY OF THE INVENTION

In one general aspect of the invention, a surgical instrument includes a cutting implement comprised of two elements spaced apart from one another along an axis. A driver rotates the two elements in opposite directions about the axis. Another aspect of the invention is a method of using such an instrument in a surgical procedure.

Among other advantages, because the two elements of the cutting implement rotate in opposite directions, the surgical instrument is easier for a user (e.g., a surgeon) to handle during surgery than an instrument having a single-element implement that rotates in only one direction. When the two-element cutting implement is brought into contact with tissue, the cutting torque applied by the driver causes each element of the implement to generate a reaction force in a direction tangential to the outer surface of the implement. Because the two elements of the implement rotate in opposite directions, these tangential forces are opposed to one another, and thus tend to cancel. This cancellation effect reduces the tendency of the implement to skip or "walk" over the surface of the tissue (particularly hard calcified tissues such as bone), making the instrument more manageable.

Preferred embodiments include the following features.

In a particularly useful embodiment, the driver includes two drive members and a transmission coupled therebetween. The transmission includes three gears, two attached to proximal regions of the respective drive members, and a third in engagement with the other two. Each of the two elements of the cutting implement (e.g., an abrader) is attached to a distal region of one of the drive members.

In another useful embodiment, the first of the two drive members extends distally from the base, and the proximal end of the second drive member lies distally of the base. A wheel in engagement with both the proximal end of the second drive member and a region of the first drive member transmits torque between the two drive members. The wheel can be comprised of rubber, and if so can serve as a torque-limiting clutch, slipping in the event the second drive member becomes jammed or otherwise bound up so that excessive torque would be required to rotate it. This torque-limiting feature can thus prevent or reduce damage to the instrument. Alternatively, the wheel can be a gear, and the proximal end of the second drive member and a region of the first drive member can be provided with mating gear teeth.

In another aspect of the present invention, the cutting element driver is disposed coaxially within an outer member that extends distally from the base along an axis. A two-element cutting implement is exposed through an opening in the outer member that extends parallel to the axis.

Among other advantages, the outer member serves as a guard to protect surrounding tissue from moving portions of the driver. The opening in the outer member exposes tissue immediately adjacent the opening to the cutting implement, thus determining the direction of cutting of the implement. Moreover, in embodiments in which the cutting implement is a shaver comprised of two blades that move toward one another, the effective blade velocity is twice that of an instrument in which either of the blades is stationary with respect to the opening in the outer member.

Other features and advantages of the invention will become apparent from the following detailed description, and from the claims.

DESCRIPTION OF THE PREFERRED EMBODIMENTS

Figure 1:
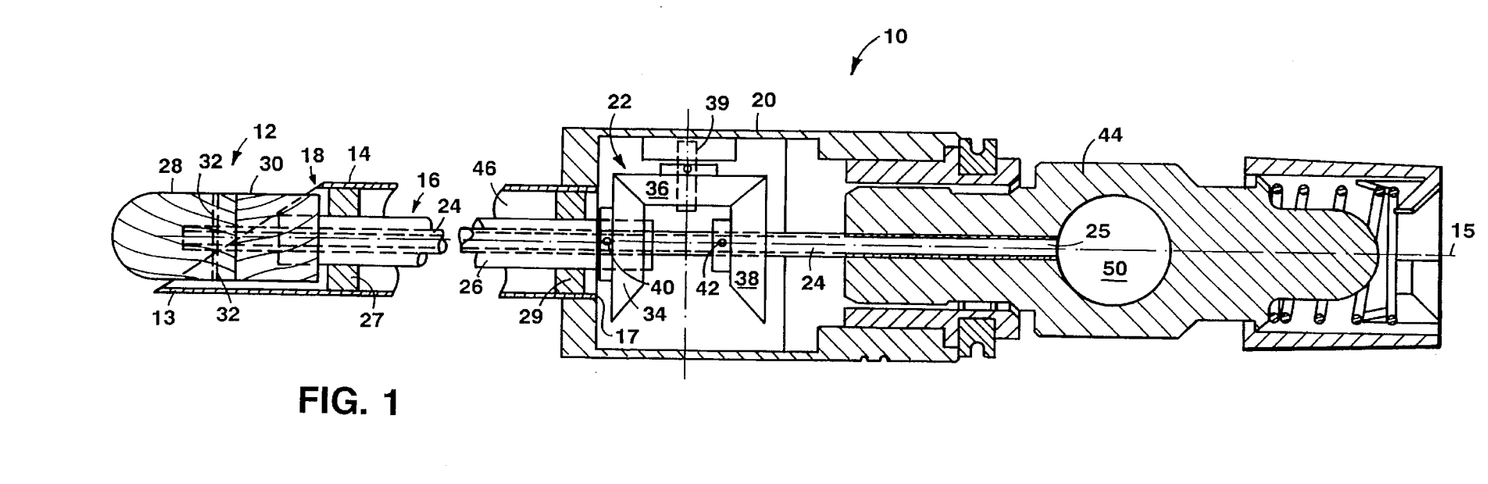
FIG. 1 is a partially cross-sectional side view, not drawn to scale, of a surgical instrument.

Referring to FIG. 1, a surgical instrument 10 suitable for performing, e.g., closed, arthroscopic surgery on the knee with a surgical tool 12, includes an outer tube 14, e.g., of stainless steel, within which a drive shaft 16 is coaxially disposed. The distal end 13 of outer tube 14 is scarf-cut at an approximately 30° angle with respect to the longitudinal axis 15 of the tube, providing an opening 18 in tube 14 that extends parallel to axis 15. Opening 18 exposes tissue immediately adjacent the opening to surgical tool 12, and thus determines the direction of cutting of the tool. The proximal end 17 of outer tube 14 is rigidly attached to a base 20 that houses a gear train 22 for driving drive shaft 16.

Drive shaft 16 includes an inner drive tube 24 coaxially and rotatably disposed within an outer drive tube 26, both of, e.g., stainless steel, and both having wall thicknesses of on the order of 0.012" (0.031 cm.). The outer diameter of inner drive tube 24 and the inner diameter of outer drive tube 26 are selected to provide a close-running fit between the two tubes so that inner tube 24 is supported by outer tube 26 as they rotate with respect to one another. For example, the outer diameter of inner drive tube 24 can be 0.136" (0.345 cm.), and the inner diameter of outer drive tube 26 can be 0.138" (0.350 cm.). The outer surface of inner tube 24 can be electropolished and plated.

The proximal end of outer drive tube 26 attaches to gear train 22, as described in further detail below. The proximal end of inner drive tube 24 rigidly attaches to a coupling 44 rotatably attached to the proximal end of base 20. The inner passage 25 extending through the length of inner drive tube 24 opens at its proximal end at a vacuum source opening 50 defined by coupling 44. Base 20 and coupling 44 fit into a handpiece 110 (FIG. 3), which includes a motor 112 for rotating inner and outer drive tubes 24, 26 with respect to one another, as well as with respect to outer tube 14. One example of such a handpiece is described in U.S. Pat. No. 4,705,038, now U.S. Pat. No. Reissue 34,556, entitled "Surgical System for Powered Instruments," assigned to the present assignee and incorporated herein by reference in its entirety.

The clearance between outer tube 14 and both surgical tool 12 and drive shaft 16 is on the order of 0.039" (0.100 cm). Drive shaft 16 is supported within outer tube 14 by a pair of bearings 27, 29, e.g., bronze bushings or heat shrink tubing sections, located just proximal of opening 18 and just distal of proximal end 17 of tube 14, respectively. Bearings 27, 29 maintain drive shaft 16 concentric with outer tube 14 as drive shaft 16 rotates. Distal-end bearing 27 also maintains the spacing between surgical tool 12 and outer tube 14 when tool 12 is laterally loaded during cutting. Bearing 27 thus reduces the likelihood that surgical tool 12 will contact and abrade away outer tube 14. In addition, distal-end bearing 27 prevents tissue fragments cut by tool 12 from entering into the annular region between outer tube 14 and drive member 16.

Surgical tool 12 is an abrader (or burr) cut with an edgeform comprising a series of circumferentially spaced, shallow fluted cutting edges for cutting hard tissue such as bone. Tool 12 includes two elements, distalmost element 28 and proximalmost element 30, arranged adjacent to one another, spaced apart along longitudinal axis 15 for relative rotation about the axis. The distal end of inner drive tube 24 is attached to distalmost element 28 of surgical tool 12, and the distal end of outer drive tube 26 is attached to proximalmost element 30 (e.g., by welding or brazing).

Figure 2:
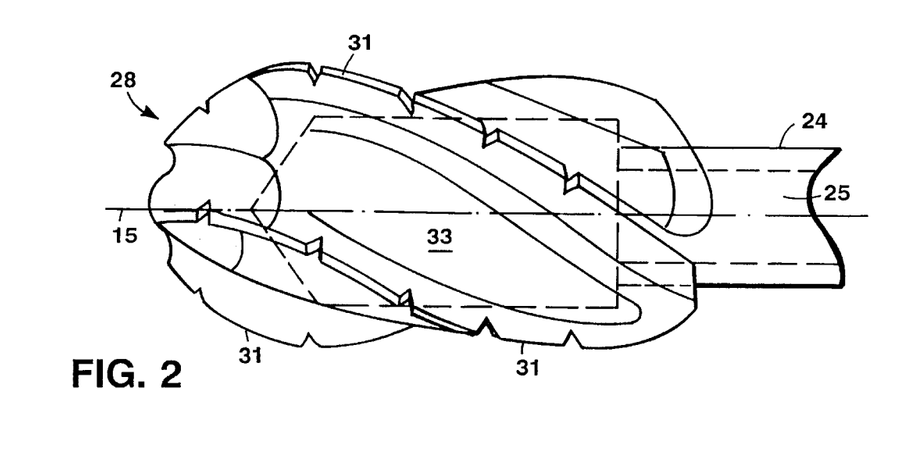
FIG. 2 shows one of the cutting elements of the surgical instrument.

Distalmost element 28 is provided with a series of radially extending through-holes 32 that communicate with inner passage 25 of inner drive tube 24. Alternatively, as shown in FIG. 2, distalmost element 28 can be "perforated" by cutting the fluted cutting edges 31 so deeply that the cuts extend into an interior chamber 33 of the element, which chamber 33 communicates with inner passage 25 of inner drive tube 24. Such a cutting element is disclosed in copending U.S. application Ser. No. 08/328,450, entitled "Surgical Instrument," filed Oct. 24, 1994, assigned to the present assignee, and incorporated herein by reference in its entirety.

Gear train 22 in base 20 includes three intermeshing bevel gears 34, 36, 38. The middle, or "idler," bevel gear 36 is rotatably attached by pivot 39 to the inner wall of base 20. The distalmost bevel gear 34 is attached to the proximal end of outer drive tube 26 by, e.g., a set screw 40, and the proximalmost bevel gear 38 is attached to a point along the length of inner drive tube 24 by, e.g., a set screw 42. Idler bevel gear 36 transmits torque between proximalmost bevel gear 38 and distalmost bevel gear 34. Because of the arrangement of gear train 22, proximalmost bevel gear 38 and distalmost bevel gear 34 rotate in opposite directions about axis 15.

Figure 3:
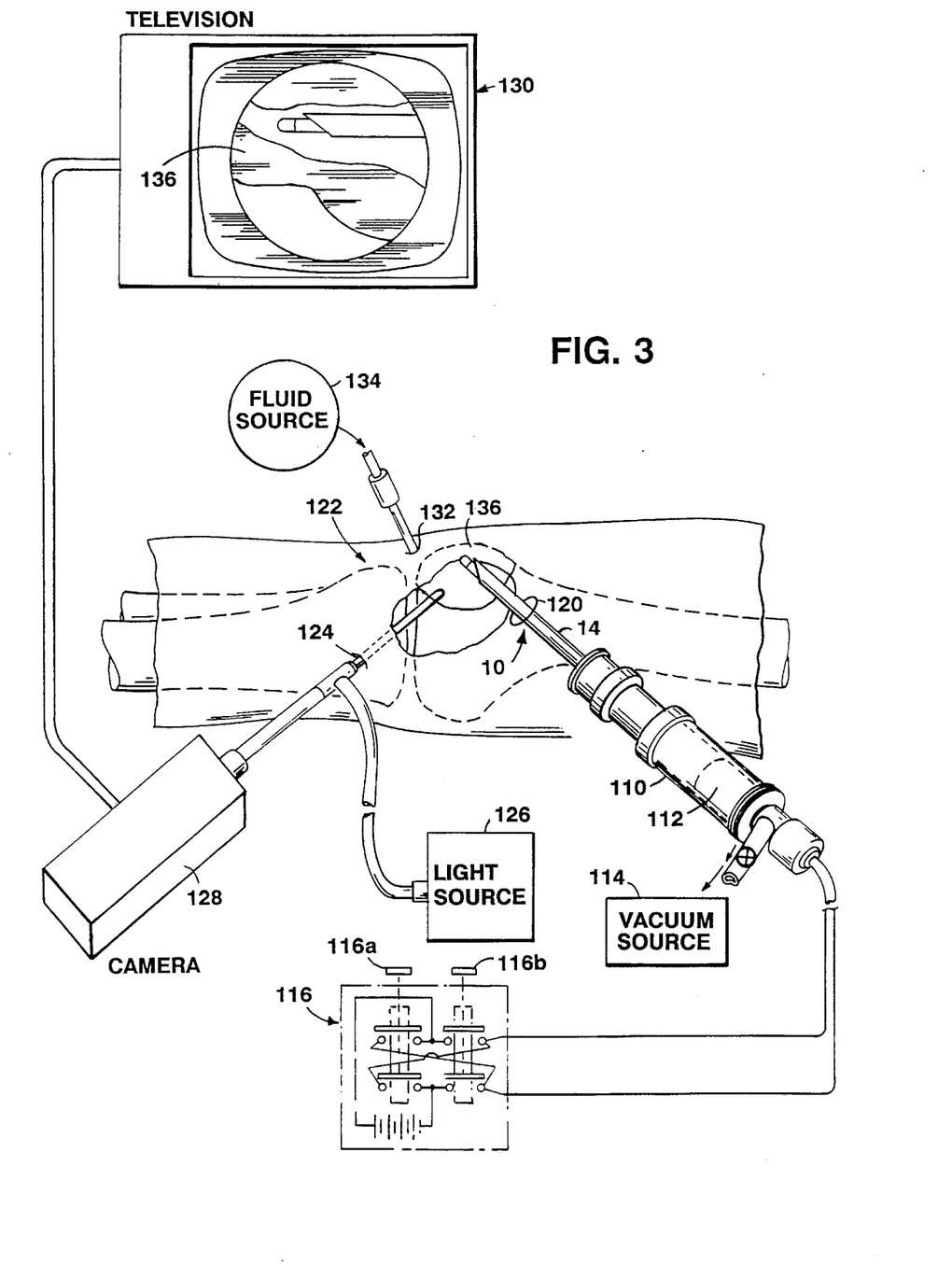
FIG. 3 shows the surgical instrument in use.

Referring also to FIG. 3, in operation, surgical instrument 10 is inserted into the distal end of a handpiece 110. Outer tube 14 is then introduced as shown through a puncture wound 120 in the patient's skin and into the knee joint 122, below the patella. Light is projected into the joint via a second puncture 124 using a fiber optic light source 126, and a visual image of the surgical site is returned through a separate optical path to a television camera 128. The image is delivered by camera 128 onto a television screen 130 for viewing by the surgeon. (Alternatively, the surgeon can view the image using an eyepiece, or the image can be recorded.)

The surgeon operates surgical tool 12 by activating motor 112, which receives operating potential and current from power supply 116. Motor 112 engages and rotates coupling 44, thereby applying torque to inner drive tube 24 and proximalmost bevel gear 38. Inner drive tube 24 transmits this torque to the distal end of instrument 10, rotating distalmost element 28 of surgical tool 12.

Through idler bevel gear 36, proximalmost bevel gear 38 drives distalmost bevel gear 34, which in turn drives outer drive tube 26. As noted above, because of the arrangement of bevel gears 34, 36, 38 in gear train 22, outer drive tube 26 and inner drive tube 24 rotate in opposite directions. Like inner drive tube 24, outer drive tube 26 transmits this torque to the distal end of instrument 10, rotating proximalmost element 30 of surgical tool 12 in a direction opposite to the direction of rotation of distalmost element 28.

The surgeon controls the rotational speed and direction (either unidirectional or oscillatory) of inner drive tube 24 using foot switches 116a, 116b, which control the magnitude and polarity of operating potential and current provided by power supply 116 to motor 112. Motor 112 is capable of rotating inner drive tube 24 over a wide range of speeds, e.g., between about 100 rpm and 5000 rpm, and can deliver a torque of up to 25 oz. inches (0.177 Nm).

Different types of surgical instruments such as instrument 10 have rotational and/or torsional limits. To prevent the surgeon from inadvertently operating instrument 10 at dangerously high speeds and/or torques, instrument 10 identifies to sensors (not shown) in handpiece 110 what type of instrument it is, and the speed of and torsion applied by motor 112 is controlled so that these limits are not exceeded. This control technique is described in the aforementioned U.S. Pat. No. 4,705,038.

During the surgical procedure, the body joint is distended with fluid introduced, through a third puncture wound 132, from a fluid source 134. The fluid irrigates the site and renders certain tissue, e.g., synovial tissue, mobile so that it floats and can be displaced by instrument 10 during the procedure (similar to the movement of seaweed in water).

The surgeon progressively cuts away tissue 136 (e.g., bone) by moving surgical instrument 10 from side to side and in the axial direction using handpiece 110 (while viewing television screen 130). When tool 12 is brought into contact with tissue 136, a reaction force is generated in a direction tangential to the outer surface of each element 28, 30 of surgical tool 12 as a result of the cutting torque applied by motor 112. Because the two elements 28, 30 of tool 12 rotate in opposite directions, these tangential forces are generated in opposite directions. And because the two elements 28, 30 of tool 12 are approximately the same size, these opposed tangential forces are of approximately the same magnitude. The opposed forces thus tend substantially to cancel each other out, reducing the tendency of tool 12 to skip or "walk" over the surface of tissue 136 (particularly hard calcified tissues such as bone). The surgeon operating tool 10 thus has a greater degree of control over the placement and handling of surgical tool 12 than if tool 12 were a single-burr implement.

During operation, a vacuum source 114 coupled to handpiece 110 applies vacuum at vacuum source opening 50 (FIG. 1). This vacuum is communicated, through inner passage 25 of inner drive tube 24, to distalmost cutting element 28, drawing irrigation fluid and body material cut by the elements 28, 30 of surgical tool 12 into through-holes 32. This material then flows back to vacuum source opening 50, where it exits instrument 10.

Other embodiments are within the scope of the following claims.

Figure 4:
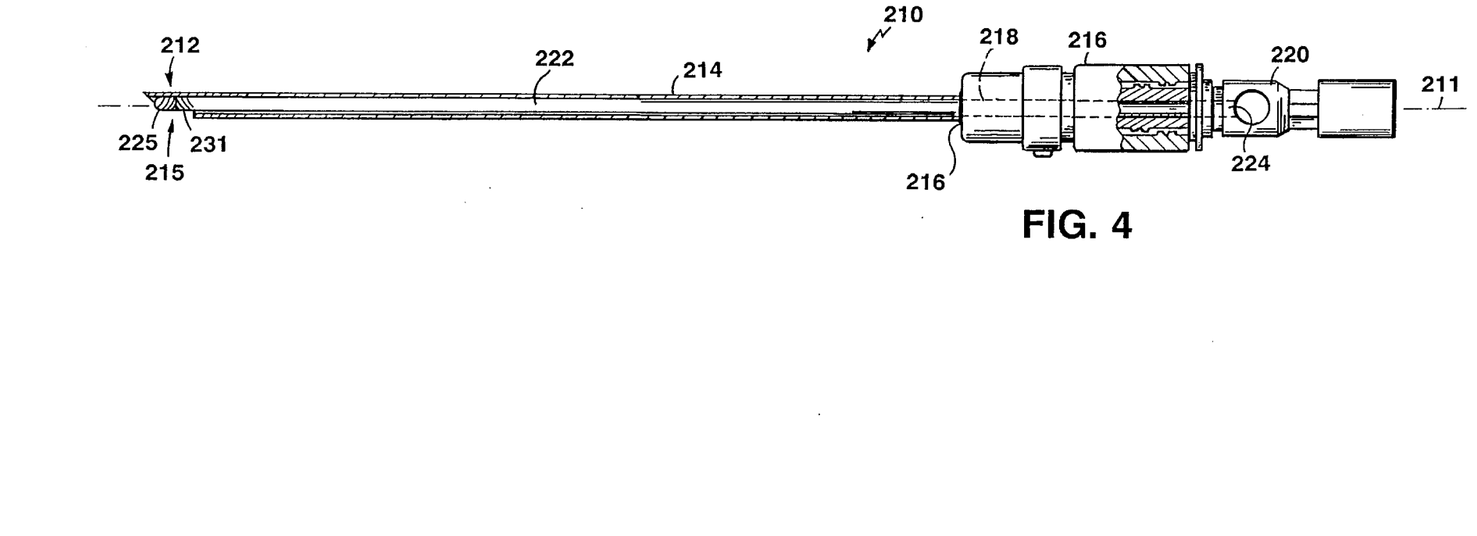
FIG. 4 is a cross-sectional side view of another surgical instrument.
Figure 5:
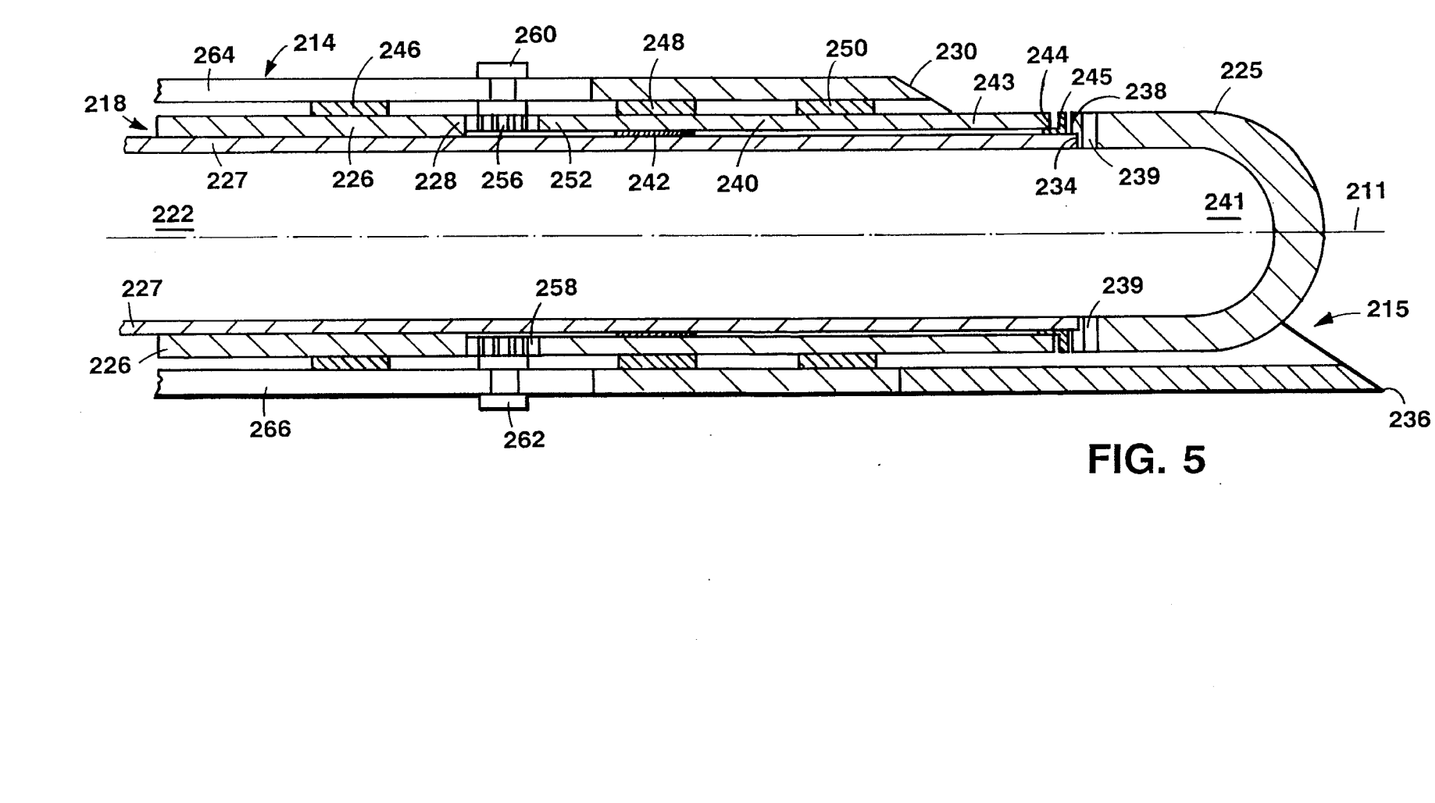
FIG. 5 is a cross-sectional side view of the distal region of the surgical instrument shown in FIG. 4.
Figure 6:
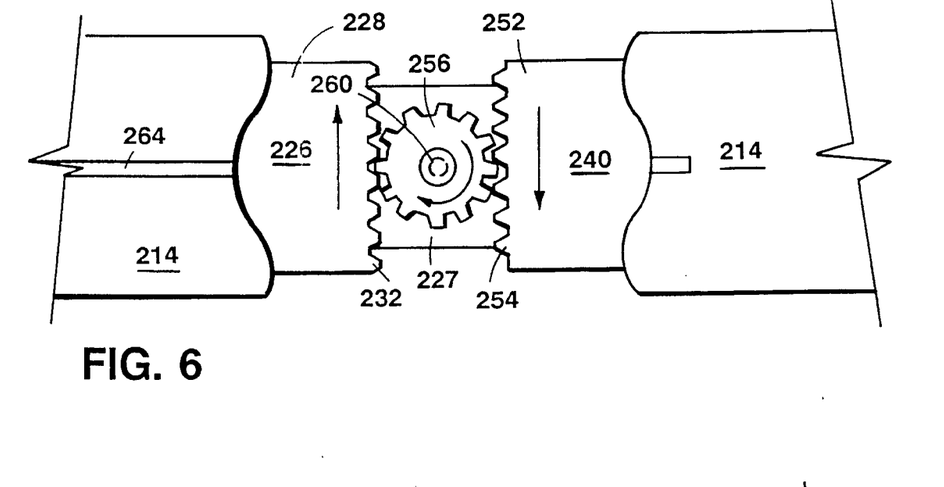
FIG. 6 is a partially broken-away top view of a portion of the surgical instrument shown in FIG. 4.

For example, another surgical instrument 210 extending along an axis 211 and carrying a two-element counter-rotating surgical tool 212 at its distal end is shown in FIGS. 4–6. Surgical instrument 210 includes a rigid, stationary outer tube 214 attached at its proximal end to a base 216. Like outer tube 14 in instrument 10 (FIG. 1), the distal end of outer tube 214 is scarf-cut at an approximately 30° angle with respect to the longitudinal axis 211 of the instrument, providing an opening 215 in tube 214 that extends parallel to axis 211.

A rotating drive assembly 218 disposed coaxially within outer tube 214 is attached at its proximal end to a coupling 220. Like coupling 44, coupling 220 fits into handpiece 110 (FIG. 3), and includes a vacuum source opening 224 in fluid communication with the inner passage 222 extending through drive assembly 218. The distal end of drive assembly 218 carries surgical tool 212, an abrader cut with an edgeform comprising a series of circumferentially spaced, shallow fluted cutting edges for cutting hard tissue such as bone.

As shown in detail in FIG. 5, drive assembly 218 includes a gear sleeve 226 welded over a distal region of a thin-walled tube 227 that extends back to the proximal end of instrument 210 and attaches at its proximal end to coupling 220 (FIG. 4). The distal end 228 of gear sleeve 226 (which defines a shoulder with tube 227) lies proximal of the proximalmost edge 230 of opening 215 in outer tube 214 and, as shown in FIG. 6, is provided with a circumferentially spaced series of gear teeth 232.

The distal end 234 of thin-walled tube 227 lies distal of the proximalmost edge 230 of opening 215 in outer tube 214, but proximal of the distalmost edge 236 of opening 215. Distalmost element 225 of tool 212 is welded to distal end 234 of tube 227. The outer diameter of distalmost element 225 is larger than the outer diameter of tube 227, such that the proximal face 238 of distalmost element 225 defines a shoulder with tube 227. Like distalmost element 28 of instrument 10, distalmost element 225 is provided with a series of radially extending through-holes 239 that extend to a hollow interior region 241 of element 225, which interior region 241 communicates with inner passage 222 of tube 227. Alternatively, distalmost element 225 can be perforated like distalmost element 28, as shown in FIG. 2. When vacuum is applied to vacuum source opening 224, tissue fragments and irrigation fluid are drawn into through-holes 239 and into inner passage 222, through which they pass out of instrument 210.

Drive assembly 218 further includes an intermediate tube 240 disposed coaxially over tube 227 between distal end 228 of gear sleeve 226 and proximal face 238 of distalmost element 225. The distal region of intermediate tube 240 (i.e., that portion of tube 240 that lies distal of proximalmost edge 230 of opening 215 in outer tube 214) is provided with a series of circumferentially spaced, shallow fluted cutting edges for cutting hard tissue such as bone, and serves as the proximalmost element 243 of tool 212.

The outer diameter of tube 227 and the inner diameter of intermediate tube 240 are selected to provide a close-running fit between the two tubes, so that tube 240 can rotate with respect to tube 227. A segment of heat-shrink tubing 242 attached over thin-walled tube 227 serves as a bearing on which intermediate tube 240 rotates with respect to tube 227. The outer surface of tube 227 may additionally or alternatively be electropolished and plated. A bronze bushing 245 (which is L-shaped in cross-section) is disposed both radially and axially between the distal end 244 of intermediate tube 240 and proximal face 238 of distalmost element 225, maintaining the spacing therebetween.

The outer diameter of intermediate tube 240 is approximately equal to the outer diameter of gear sleeve 226 and distalmost element 225. A heat-shrink tubing segment 246 attached over gear sleeve 226 and two heat-shrink tubing segments 248, 250 attached over intermediate tube 240 serve as radial space-maintaining bearings between drive assembly 218 and outer tube 214, allowing sleeve 226 and intermediate tube 240 to rotate with respect to outer tube 214.

As shown in FIG. 6, like distal end 228 of gear sleeve 226, the proximal end 252 of intermediate tube 240 is provided with a circumferentially spaced series of gear teeth 254. Gear teeth 232, 254 mesh with pinion gears 256, 258 disposed between distal end 228 of gear sleeve 226 and proximal end 252 of intermediate tube 240. Shafts 260, 262 extend radially outward from pinion gears 256, 258, and a reduced-diameter region of each of shafts 260, 262 passes through respective slots 264, 266 in outer tube 214. Slots 264 extend to the distal end of outer tube 214. This gear train arrangement transmits torque between thin-walled tube 227 (through gear sleeve 226) and intermediate tube 240, causing tubes 227, 240—and thus also distalmost element 225 and proximalmost element 243 of tool 212—to rotate in opposite directions when tube 227 is rotated, as indicated by the arrows shown in FIG. 6.

To assemble instrument 210, distalmost element 225 is first welded onto distal end 234 of tube 227. Heat-shrink tubing segment 242 is then attached over thin-walled tube 227, and bushing 245 and intermediate tube 240 are slid over the proximal end of tube 227 until they abut proximal face 238 of element 225. Gear sleeve 226 is then also slid over the proximal end of tube 227 and welded into place, after which heat-shrink tubing segments 246, 248, 250 are then attached over gear sleeve 226 and intermediate tube 240. Pinion gears 256, 258 are then fitted into the gap between distal end 228 of gear sleeve 226 and proximal end 252 of intermediate tube 240. The entire drive assembly 218 then slid into the proximal end of outer tube 214, with shafts 260, 262 traveling in slots 264, 266.

Figure 7:
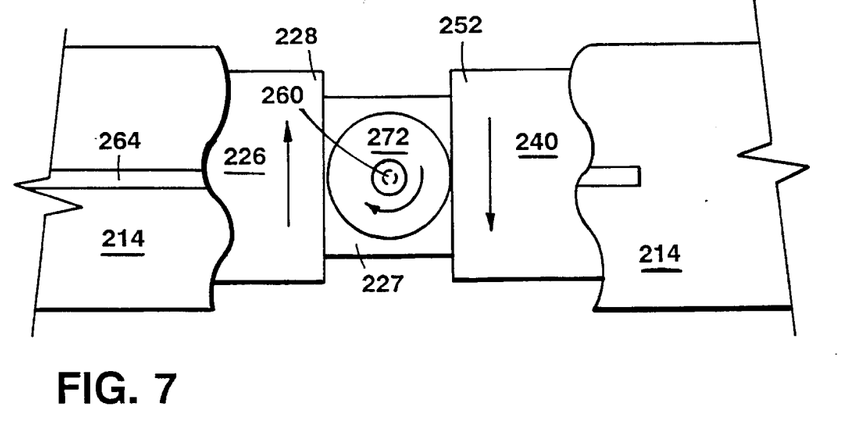
FIG. 7 is a partially broken-away top view of a portion of another embodiment of the surgical instrument shown in FIG. 4.

An alternate transmission mechanism to the gear train arrangement described above is shown in FIG. 7. In this transmission, distal end 228 of gear sleeve 226 and proximal end 252 of intermediate tube 240 are both smooth, and rubber wheels 272 (only one shown in FIG. 7) have been substituted for gears 256, 258. The frictional engagement between wheels 272 and the smooth abutting faces of sleeve 226 and intermediate tube 240 causes intermediate tube 240 and thin-walled tube 227 to rotate in opposite directions. Moreover, should intermediate tube 240 become jammed or otherwise bound up so that excessive torque would be required to rotate it, rubber wheels 272 will slip, serving as torque-limiting clutches that could prevent damage to instrument 210.

Figure 8:
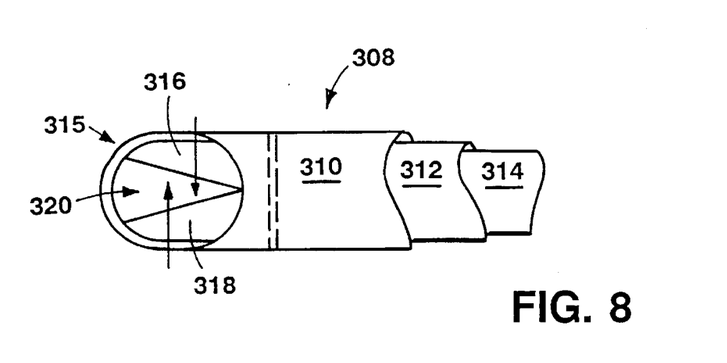
FIG. 8 is a partially broken-away side view of the distal region of another embodiment of the surgical instrument shown in FIG. 4.

The distal region of another embodiment of the invention, surgical instrument 308, is shown in FIG. 8. As with the instruments 10, 210 discussed above, surgical instrument 308 includes an outer tube 310, an intermediate tube 312, and an inner tube 314. Intermediate tube 312 carries a first element of a shaver 315, blade 316, at its distal end, and inner tube 314 carries a second element of shaver 315, blade 318, at its distal end. Blade 318 is coaxially disposed within blade 316. The clearance between the inner surface of blade 316 and the outer surface of blade 318 is less than that between the inner surface of intermediate tube 312 and the outer surface of inner tube 314. The edges of blades 316, 318 are thus very closely juxtaposed, providing for good cutting, and the somewhat larger clearance between intermediate tube 312 and inner tube 314 reduces the amount of friction between the two tubes as they rotate.

The edges of blades 316 and 318 are obliquely angled with respect to one another. When intermediate and inner tubes 312, 314 are counter-rotated using any of the mechanisms discussed above, the edges of blades 316, 318 move toward and closely past one another, severing tissue projecting into instrument 308 through a window 320 located near the distal end of outer tube 310. Because both blades 316, 318 move with respect to window 320, the effective blade velocity is twice that of an instrument in which either blade 316, 318 is stationary with respect to window 320. The rotations of tubes 312, 314 are synchronized so that the edges of blades 316, 318 move past one another as they are exposed through window 320, as shown in FIG. 8.

Although the surgical instruments described above are straight between their proximal and distal ends, a surgical instrument embodying the teachings disclosed herein could instead include a bend region (e.g., in the rigid outer tube) to angularly offset the surgical tool from the generally straight axis of the instrument. To transmit torque through the bend region in the outer tube to operate the surgical tool, the inner and outer drive members 24, 26 (surgical instrument 10) or the inner and intermediate tubes 227, 240 (surgical instrument 210) could be flexible, at least in the bend region. (In surgical instrument 210, if intermediate tube 240 does not extend all the way to the bend region, it can instead be rigid along its length.) Various tube configurations exhibit the requisite flexibility and torque-carrying capability to be employed in a bent surgical instrument. For instance, a region of an otherwise rigid tube or tubes may be relieved with a series of axially spaced, circumferentially extending slots. Slotting a rotatable tube for flexibility and torque transmission is described in U.S. Pat. No. 5,152,744, assigned to the present assignee and incorporated herein by reference in its entirety. The flexible region or regions could instead be comprised of a series of discrete, interengaging segments, as disclosed in copending application Ser. No. 08/228,083, filed on Apr. 15, 1994, which is assigned to the present assignee and incorporated herein by reference in its entirety. Alternatively, the tubes could be comprised, at least in the bend region, of a flexible or elastomeric material, such as rubber, plastic, or other polymer.

Other types of surgical tools, apart from abraders and blades, may be employed with any of surgical instruments 10, 210, 310. Moreover, the elements of the surgical tool may be removably connected to the distal ends of their respective drive members (e.g., the inner and outer drive members 24, 26 in surgical instrument 10 or the inner and intermediate tubes 227, 240 in surgical instrument 210), allowing just the elements of the surgical tool to be replaced should they become worn or damaged. Removably coupling a surgical tool to the distal end of a drive member is disclosed in U.S. Pat. No. 5,320,635, assigned to the present assignee and incorporated herein by reference in its entirety. Also, the surgical tool elements and their respective drive members need not be comprised of the same material. Rather, the surgical tool elements can be comprised of a hard material well-suited to cutting, and the drive members of a more compliant material for, e.g., transmitting torque through a bend region.

In addition, the surgical tool elements need not counter-rotate with respect to one another, but could instead, e.g., slide in opposite directions.

While the invention has been described in terms of surgical instruments for arthroscopy, the invention may also be used with other types of instruments, for example, instruments configured for other kinds of endoscopic procedures and for biopsy applications.

What is claimed is:

1. A surgical instrument comprising:
   a base;
   a driver extending distally from said base; and
   a cutting implement disposed along an axis and carried at a distal region of said driver, said cutting implement including first and second cutting elements;
   said driver being configured to transmit force applied at said base to said cutting implement to rotate said first cutting element about said axis in a first direction and to rotate said second cutting element about said axis in a second direction opposite to said first direction, said first and second cutting elements being arranged so that (1) at least a portion of said first cutting element is exposed for cutting whenever said first element rotates in said first direction and (2) at least a portion of said second cutting element is exposed for cutting whenever said second element rotates in said second direction.

2. The surgical instrument of claim 1 wherein said driver comprises a first drive member and a second drive member.

3. The surgical instrument of claim 2 wherein said first cutting element is attached to said first drive member and said second cutting element is attached to said second drive member.

4. The surgical instrument of claim 3 wherein said driver comprises a transmission coupled between said first drive member and said second drive member, said transmission being configured to rotate said first drive member in said first direction when said second drive member rotates in said second direction.

5. The surgical instrument of claim 4 wherein said first drive member and said second drive member both extend distally from said base.

6. The surgical instrument of claim 4 wherein said first drive member extends distally from said base and a proximal end of said second drive member is disposed distal of said base.

7. The surgical instrument of claim 1 wherein said cutting implement is an abrader.

8. The surgical instrument of claim 1 further comprising a tissue evacuation passage extending distally from said base through said driver and opening in the region of said first cutting element.

9. The surgical instrument of claim 1 further comprising a stationary member extending distally from said base, said stationary member carrying said driver.

10. The surgical instrument of claim 9 wherein said portion of said first cutting element is exposed for cutting through an opening in said stationary member.

11. The surgical instrument of claim 10 wherein said portion of said second cutting element is exposed for cutting through said opening in said stationary member.

12. A surgical instrument comprising:
   a base;
   a driver extending distally from said base, said driver having a first drive member extending distally from said base and a second drive member extending distally from said base; and
   a cutting implement disposed along an axis and carried at a distal region of said driver, said cutting implement including first and second cutting elements spaced apart from one another along said axis, said first cutting element being attached to said first drive member and said second cutting element being attached to said second drive member;
   said driver being configured to transmit force applied at said base to said cutting implement, said driver having a transmission comprising a first gear attached to said first drive member, a second gear attached to said second drive member, and a third gear in engagement with said first gear and said second gear, said gears being configured to rotate said second drive member about said axis in one direction when said first drive member rotates about said axis in the opposite direction in response to said force.

13. A surgical instrument comprising:
   a base;
   a driver extending distally from said base, said driver having a first drive member and a second drive member, said first drive member extending distally from said base and a proximal end of said second drive member being disposed distal of said base; and
   a cutting implement disposed along an axis and carried at a distal region of said driver, said cutting implement including first and second cutting elements spaced apart from one another along said axis, said first cutting element being attached to said first drive member and said second cutting element being attached to said second drive member;
   said driver being configured to transmit force applied at said base to said cutting implement, said driver having a transmission comprising a wheel in engagement with both said proximal end of said second drive member and a region of said first drive member, said wheel being configured for use in rotating said second drive member about said axis in one direction when said first drive member rotates about said axis in the opposite direction in response to said force.

14. The surgical instrument of claim 13 wherein said wheel is comprised of rubber.

15. The surgical instrument of claim 13 wherein said wheel is a gear, and wherein said proximal end of said second drive member and said region of said first drive member are provided with gear teeth.

16. A surgical instrument comprising:
   a base;
   a first member extending distally from said base along an axis, said first member having an opening that extends parallel to said axis;
   a driver disposed coaxially within said first member and extending distally from said base; and
   a cutting implement carried by said driver and exposed through said opening in said first member, said cutting implement including first and second cutting elements;
   said driver being configured to transmit force applied at said base to said cutting implement to move said first cutting element in a first direction and to move said second cutting element in a second direction opposite to said first direction.

17. The surgical instrument of claim 16 wherein said driver comprises a first drive member and a second drive member.

18. The surgical instrument of claim 17 wherein said first cutting element is attached to said first drive member and said second cutting element is attached to said second drive member.

19. The surgical instrument of claim 18 wherein said driver comprises a transmission coupled between said first drive member and said second drive member, said transmission being configured to move said first drive member in said first direction when said second drive member moves in said second direction.

20. The surgical instrument of claim 19 wherein said first drive member and said second drive member both extend distally from said base.

21. The surgical instrument of claim 19 wherein said first drive member extends distally from said base and a proximal end of said second drive member is disposed distal of said base.

22. The surgical instrument of claim 16 wherein said axis of said first member is straight.

23. The surgical instrument of claim 16 wherein said cutting implement is an abrader.

24. The surgical instrument of claim 16 wherein said cutting implement is a shaver.

25. A surgical instrument comprising:
   a base;
   a stationary member extending distally from said base, a portion of said stationary member lying distally of said base being configured for insertion through a puncture wound in a surgical procedure;
   a first drive member carried by said stationary member and extending distally from said base;
   a second drive member carried by said stationary member, said second drive member terminating at a proximal end disposed distal of said base along said portion of said stationary member lying distally of said base, said second drive member being rotatable with respect to said first drive member;
   a cutting implement including a first cutting element attached to said first drive member and a second cutting element attached to said second drive member; and
   a transmission coupled between said first drive member and said second drive member, said transmission being configured to rotate said second drive member in one direction when said first drive member rotates in the opposite direction in response to a force applied at the base.

26. The surgical instrument of claim 25 wherein said cutting implement is an abrader.

27. The surgical instrument of claim 25 wherein said cutting implement is a shaver.

28. The surgical instrument of claim 25 further comprising an outer tube extending distally from said base, said outer tube having an opening in a distal region thereof.

29. The surgical instrument of claim 28 wherein said cutting implement is exposed through said opening in said outer tube.

30. The surgical instrument of claim 28 wherein said first drive member is disposed within said outer tube and is rotatable with respect to said outer tube.

31. The surgical instrument of claim 28 wherein said second drive member is disposed within said outer tube and is rotatable with respect to said outer tube.

32. A surgical instrument comprising:
   a base;
   a first drive member extending distally from said base;
   a second drive member having a proximal end disposed distal of said base, said second drive member being rotatable with respect to said first drive member;
   a cutting implement including a first cutting element attached to said first drive member and a second cutting element attached to said second drive member; and
   a transmission comprising a wheel in engagement with both said proximal end of said second drive member and a region of said first drive member, said wheel being configured for use in rotating said second drive member in one direction when said first drive member rotates in the opposite direction.

33. The surgical instrument of claim 32 wherein said wheel is comprised of rubber.

34. The surgical instrument of claim 32 wherein said wheel is a gear, and wherein said proximal end of said second drive member and said region of said first drive member are provided with gear teeth.

35. A method of surgery for a joint space comprising:
   introducing into said joint from outside said joint via a puncture wound in the flesh:
      a first conduit for introducing fluid from a fluid source;
      a visualization instrument; and
      a surgical instrument comprising:
         a base;
         a driver extending distally from said base;
         a cutting implement disposed along an axis and carried at a distal region of said driver, said cutting implement including first and second cutting elements;
         said driver being configured to transmit force applied at said base to said cutting implement to rotate said first cutting element about said axis in a first direction and to rotate said second cutting element about said axis in a second direction opposite to said first direction, said first and second cutting elements being arranged so that (1) at least a portion of said first cutting element is exposed for cutting whenever said first element rotates in said first direction and (2) at least a portion of said second cutting element is exposed for cutting whenever said second element rotates in said second direction;
   introducing fluid through said first conduit into said joint to distend said joint and to provide a clear field for viewing through said visualization instrument;
   positioning said visualization instrument to enable observation of an area of said joint to be surgically treated, and
   on the basis of said visual observation, positioning said surgical instrument adjacent to said area of said joint and applying a force at said base to said driver to rotate said first and second cutting elements to cut tissue exposed to said cutting implement.

36. A surgical instrument comprising:
   a base;
   a driver extending distally from said base; and
   a cutting implement disposed along an axis and carried at a distal region of said driver, said cutting implement comprising
      a first cutting element having a cutting edge located a first radial distance from said axis; and
      a second cutting element having a cutting edge located a second radial distance from said axis, said second radial distance being substantially equal to said first radial distance;
      said driver being configured to transmit force applied at said base to said cutting implement to rotate said first cutting element about said axis in one direction and said second cutting element about said axis in the opposite direction.

37. A surgical instrument comprising:
   a base;
   a driver extending distally from said base; and
   a cutting implement disposed along an axis and carried at a distal region of said driver, said cutting implement including first and second cutting elements;
   said driver being configured to transmit force applied at said base to said cutting implement to rotate said first cutting element about said axis in a first direction and to rotate said second cutting element about said axis in a second direction opposite to said first direction, said first and second cutting elements being arranged so that at least a portion of each element remains exposed for cutting at a cutting region while said first and second cutting elements rotate through a full rotation.

38. A surgical instrument comprising:
   a base;
   a driver extending distally from said base; and
   a cutting implement disposed along an axis and carried at a distal region of said driver, said cutting implement including first and second cutting elements, said first cutting element having a distal surface opposing a proximal surface of said second cutting element;
   said driver being configured to transmit force applied at said base to said cutting implement to rotate said first cutting element about said axis in a first direction and to rotate said second cutting element about said axis in a second direction opposite to said first direction.

39. A surgical instrument comprising:
   a base;
   a driver extending distally from said base; and
   a cutting implement disposed along an axis and carried at a distal region of said driver, said cutting implement including first and second cutting elements;
   said driver being configured to transmit force applied at said base to said cutting implement to rotate said first cutting element about said axis in a first direction and to rotate said second cutting element about said axis in a second direction opposite to said first direction;
   said first cutting element including a plurality of cutting edges disposed around its circumference, said cutting edges of said first cutting element being configured to cut tissue when said first cutting element is rotated in said first direction;
   said second cutting element including a plurality of cutting edges disposed around its circumference, said cutting edges of said second cutting element being configured to cut tissue when said second cutting element is rotated in said second direction.

* * * * *